United States Patent [19]

Potts

[11] Patent Number: 4,476,313

[45] Date of Patent: Oct. 9, 1984

[54] PYRYLIUM SALTS

[75] Inventor: Kevin T. Potts, Schenectady, N.Y.

[73] Assignee: Rensselaer Polytechnic Institute, Troy, N.Y.

[21] Appl. No.: 494,392

[22] Filed: May 13, 1983

Related U.S. Application Data

[62] Division of Ser. No. 364,893, Apr. 2, 1982, Pat. No. 4,451,659.

[51] Int. Cl.³ .................. C07D 309/34; C07D 311/30
[52] U.S. Cl. ................................. 549/213; 549/403; 549/416
[58] Field of Search ............... 549/4, 213, 60, 401, 549/403, 414, 416, 421; 546/256, 268, 283, 284

[56] References Cited

U.S. PATENT DOCUMENTS 3,617,268 11/1971 Murakami et al. ............. 549/403 X
3,896,112 7/1975 Kubota et al. .................. 549/403 X

OTHER PUBLICATIONS

Huenig et al., Chemical Abstracts, vol. 82 (1975) 4099e.
Potts et al., Jacs. vol. 103 (1981), pp. 3585-3586.

Primary Examiner—Richard L. Raymond
Attorney, Agent, or Firm—McGlew and Tuttle

[57] ABSTRACT

A method is disclosed for preparing pyrylium and thiapyrylium salts having the formula represented below (where X is O, S or Se):

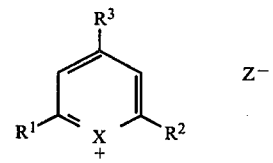

and where $R^1$ and $R^2$ represents a branched or unbranched alkyl radical having up to about 15 carbon atoms, an aromatic group having as substituents alkyl radicals with 1 to about 15 carbon atoms, alkoxy radicals having 1 to about 4 carbon atoms, substituted amino radicals have 1 to 2 carbon radicals containing 1 to about 4 carbon atoms, an heterocyclic group having as substitute alkyl radicals with 1 to about 15 carbon atoms, alkoxy radicals having 1 to about 4 carbon atoms and amino radicals having 1 or 2 carbon radicals containing 1 to about 4 carbons, thiophene radicals and furan radical containing a variety of substituents; $R^3$ represents a thioalkyl radical having 1 to about 4 carbon atoms thiobenzyl, thioaryl and thiocycloalkyl, as well as thiohetaryl radicals such as thiohydridyl and related 5-and-membered systems; and $Z^-$ is an anionic function. The salts are prepared by condensing the methyl ketone with carbon disulfide in the presence of sodium hydride, treating the product with methyl iodide to form the α-oxoketenedithioacetal; condensing the α-oxoketenedithioacetal with another methyl ketone in the presence of two equivalents of potassium tert-butoxide to form a 1,5-enedione; and cyclizing the enedione with tetrafluoroboric acid.

3 Claims, No Drawings

PYRYLIUM SALTS

FIELD AND BACKGROUND OF THE INVENTION

This is a division of application Ser. No. 364,893 filed Apr. 2, 1982, U.S. Pat. No. 4,451,659.

The disclosed invention is a simplified method of producing known and previously unavailable pyrylium, thiopyrylium, and seleninium salts. The method produces those types of salts which have a displaceable substituent in the 4-position which allows the attachment of such salts, by displacement of this group, to a variety of organic substrates or supports. The process utilizes readily available starting materials and reaction conditions which are suitable for industrial scale use. A feature of the method and the salts produced by the method is the incorporation in the 4-position of the pyrylium and thiopyrylium salts, of a group readily displaceable by nucleophiles. This permits the attachment of the salts to an inert organic polymeric support such as cross-linked polystyrene.

Pyrylium salts are used in commercial photocopying devices and thus have wide spread application.

It is known that such salts enhance the efficiency and effectiveness of photoconductive compositions. See U.S. Pat. No. 3,938,994 to Reynolds et al; U.S. Pat. No. 3,615,396 to Gramza et al; and U.S. Pat. No. 3,250,615 to Van Allan et al.

Various techniques are known for the preparation of pyrylium and related salts. Such techniques are related to methods of preparing a larger class of substituted pyridines which contains the class of pyrylium salts.

Among the numerous ways to prepare substituted pyridines described in the literature, [see Klingsberg, E., "The Chemistry of Heterocyclic Compounds. Vols. I–III. Pyridine and its Derivatives," Interscience Publishers, New York, 1960 and Abramovitch, R., "The Chemistry of Heterocyclic Compounds. Supplement to Pyridine and its Derivatives." Wiley-Interscience New York, 1978] a noteworthy example is the use of organolithium compounds for the preparation of arylpyridines [see Ziegler, L.; Zeiser, H. Ber., 1930, 63, 1847; Overberger, G. C.; Lombardino, J. G.; Hiskey, R. G. J. Amer. Chem. Soc. 1957, 79, 6430; Bryce, D.; Skinney, A. C. J. Chem. Soc. 1963, 577], 2,2'-dipyridinyls [see Newkome, G. R.; Hager, D. C. J. Amer. Chem. Soc. 1978, 100, 5567; Parks, J. E.; Wagner, B. E.; Holm, R. H. J. Organomet. Chem. 1973, 56, 53] and 2,2',2"-terpyridinyl [see Kauffman, T.; Konig, J.; Woltermann A. Chem. Ber. 1976 109, 3864] and the application of pyridinium phenacylides or their salts in the synthesis of a wide variety of 2,4,6-trisubstituted pyridines [see Kröhnke, F. Synthesis 1976, 1; Tewari, R. S.; Misra, N. K.; Dubey, A. K. J. Heterocyclic Chem. 1980, 17, 953 and earlier references]. This last procedure has been applied to the synthesis of numerous substituted di-, tri-, quater-, quinque-, sexi- and septipyridinyls, all of which are of interest as ligands for metal chelation. 2,2'-Di- and 2,2',2"-terpyridinyl have attracted the most attention in this respect [see Wilkins, C. J.; Douglas, J. E. Inorg. Chim. Acta, 1969, 3, 635], and the 4'-(4-methoxyphenyl) terpyridinyl [see Deggau, E.; Kröhnke, F.; Schnalke, K. E.; Staudinger, H. J.; Weiss, W. Z. Klin. Chem., 1965 3, 222], and its sulfonated [see Schmidt, R.; Weis, W.; Klingmuller, V.; Staudinger, H. J., Z. Klin. Chem., 1967, 5, 308] derivative have been introduced in clinical chemistry for the estimation of $Fe^{2+}$.

In general these oligopyridines are high melting products and are difficult to dissolve in the usual organic solvents. These factors have somewhat restricted their further development. According to the present invention, a versatile, direct synthesis of a variety of substituted pyridines and oligopyridines is described, which compounds have favorable solubility characteristics.

In particular the invention discloses hitherto unknown pyrylium and thiopyrylium, and a method of preparing the same.

SUMMARY OF THE INVENTION

This invention relates to a convenient and practical synthesis of a variety of pyrylium (where X is oxygen), and consequently thiopyrylium (X is sulfur) and seleninium (X is selenium) salts of general formula I:

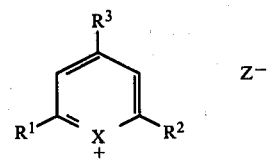

Where $R^1$ and $R^2$ represent an alkyl radical such as methyl, having up to about 15 carbon atoms, either in a normal or branched chain; an aromatic group such as a phenyl radical, or substituted phenyl radical having, as substituents, alkyl radicals with from 1 to about 15 carbon atoms, alkoxy radicals having 1 to about 4 carbon atoms, substituted amino radicals have 1 or 2 carbon radicals and containing 1 to about 4 carbon atoms; a heterocyclic group such as pyridine or substituted pyridine radical having, as substituents, alkyl radicals with 1 to about 15 carbon atoms, alkoxy radicals having 1 to about 4 carbon atoms, and amino radicals having 1 or 2 carbon radicals containing 1 to about 4 carbon atoms, as well as thiophene radicals and furan radicals. $R^3$ represents thioalkyl radical having 1 to about 4 carbon atoms, thiobenzyl, thioaryl and thiocycloalkyl radicals, as well as thioheteryl radicals such as 2-thiopylidyl and related 5- and 6-membered systems.

Z is an anionic function including such ions as tetrafluorborate, perchlorate, methanesulfonate, and halogeno ions such as bromide, iodide, chloride, fluoride and the like.

Another object of the invention is to provide a novel class of compounds which are used as sensitisers for photosensitive systems and which produce a marked increase in sensitivity at longer wavelengths of the visible light spectrum.

A further object of the invention is to provide marked versatility in the substituents incorporated into these pyrylium salts and at the same time provide a direct and efficient synthesis of these salts.

In particular, these pyrylium and thiopyrylium salts are prepared by a novel method involving the steps of: condensing a methyl ketone with carbon disulfide in the presence of sodium hydride; treating the resulting product with methyl iodide to form the α-oxoketenedithioacetal; condensing the α-oxoketenedithioacetal with another methyl ketone in the presence of two equivalents of potassium tert-butoxide to form a 1,5-enedione; and cyclizing the enedione with tetrafluoroboric acid.

Other strong bases like potassium tert-butoxide, sodium or potassium hydroxide may be used to generate the enolate of the methyl ketone for reaction with carbon disulfide and a variety of non-protic solvents, such as dimethylformamide, dimethylsulfoxide, toluene, benzene, etc. or mixtures of these solvents may be used. Alkylation of the di-thiocarboxylate di-anion occurs readily with a variety of alkyl halides or dialkyl sulfates.

An additional novel feature of the reaction is the use of two equivalents of potassium tert-butoxide in the formation of the 1,5-enedione, resulting in its isolation as its potassium salt with subsequent conversion into the neutral product. This greatly facilitates the ease of isolation of the 1,5-enedione as well as suppresses side reactions.

In this novel preparation of pyrylium salts, two methods may be utilized. In the first method, the 1,5-enedione is actually isolated prior to cyclization and in the second method, generation of the 1,5-enedione and ring closure to the pyrylium salt are actually carried out sequentially in one reaction vessel.

The various features of novelty which characterize the invention are pointed out with particularity in the claims annexed to and forming a part of this disclosure. For a better understanding of this invention, its operating advantages and specific objects attained by its uses, reference is made to the accompanying descriptive material in which preferred embodiments of the invention are illustrated.

DESCRIPTION OF THE PREFERRED EMBODIMENTS

According to one embodiment of the invention, the method used is a "one-pot", two component procedure involving the in situ generation of unsaturated 1,5-diketones derived by a reaction of α-ketoketenedithioacetals and methyl ketone carbanions. Examples shown in Table I. Reaction of these enediones with ammonium acetate in hot acetic acid gives 2,6-disubstituted-4-methylthiopyridines having general formula G. A representative selection of examples of this procedure, is shown in the Table II. Alternatively, the 1,5-enedione may be isolated before conversion into the pyridine although, in general, this offers no advantages over the more direct procedure. The synthesis of 2,2′,2″-terpyridinyl (product C in reaction I where R=R$^1$=2-C$_5$H$_4$N; R$^2$=H; X=N) illustrates the general procedure used. In Table I the SCH$_3$ group can alternately be the groups designated R$_3$ above.

TABLE I

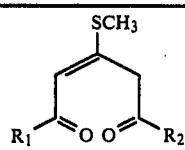

1,5-Enediones Derived from α-Oxoketene Dithioacetals

| Substituent | | Mp °C. | Yield % | Crystal Habit | Mol Formula | M.+ Rel Int | Analysis Calcd | | |
|---|---|---|---|---|---|---|---|---|---|
| R$_1$ | R$_2$ | | | | | | C | H | N |
| C$_6$H$_5$ | C$_6$H$_5$ | 106–108 | 76 | Pale Yellow Prisms (Benzene/Pot.Ether) | C$_{18}$H$_{16}$O$_2$S | 296 (7) | 72.96 | 5.44 | |
| C$_6$H$_5$ | 2-C$_4$H$_3$S | 116–118 | 61 | Pale Yellow Needles (Benzene/Pet.Ether) | C$_{16}$H$_{14}$O$_2$S$_2$ | 302 (8) | 63.57 | 4.67 | |
| C$_6$H$_5$ | 2-C$_5$H$_4$N | 124–125 | 58 | Colorless Needles (Cyclohexane) | C$_{17}$H$_{15}$NO$_2$S | 248 (2) | 68.67 | 5.08 | 4.71 |
| 2-C$_4$H$_3$S | 2-C$_4$H$_3$S | 164–165 | 70 | Pale Yellow Prisms | C$_{14}$H$_{12}$O$_2$S$_3$ | 308 (7) | 54.55 | 3.92 | |
| 2-C$_4$H$_3$O | 2-C$_4$H$_3$S | 140–142 | 47 | Pale Yellow Needles (Benzene/Pet.Ether) | C$_{14}$H$_{12}$O$_3$S$_2$ | 292 (11) | 57.54 | 4.14 | |
| 2-C$_5$H$_4$N | 2-C$_5$H$_4$N | 120–122 | 13 | Pale Yellow Prisms (Pet.Ether) | C$_{16}$H$_{14}$N$_2$O$_2$S | 298 (1) | 64.42 | 4.73 | 9.39 |
| 2-C$_5$H$_4$N | 2-C$_4$H$_5$S | 102–104 | 60 | Colorless Prisms (Benzene/Cyclohexane) | C$_{15}$H$_{13}$NO$_2$S$_2$ | 303 (1) | 59.40 | 4.32 | 4.62 |
| 3-BrC$_6$H$_4$ | 3-BrC$_6$H$_4$ | 118–119 | 81 | Colorless Needles (Methanol) | C$_{18}$H$_{14}$Br$_2$O$_2$S | 454 (3) | 47.60 | 3.11 | |
| 4-CH$_3$OC$_6$H$_4$ | 4-CH$_3$OC$_6$H$_4$ | 159–161 | 100 | Yellow Needles (Benzene) | C$_{20}$H$_{20}$O$_4$S | 356 (20) | 67.40 | 5.66 | |
| 4-CH$_3$OC$_6$H$_4$ | CH$_3$ | 106–107 | 42 | Colorless Needles (Methanol/Ether) | C$_{14}$H$_{16}$O$_3$S | 264 (18) | 63.61 | 6.10 | |
| 2-C$_4$H$_3$S | 5-Cl—2-C$_4$H$_2$S | 134–134.5 | 75 | Pale Yellow Prisms (Benzene) | C$_{14}$H$_{11}$ClO$_2$S$_3$ | 342 (10) | 49.04 | 3.23 | |
| 5-Br—2-C$_4$H$_2$S | 5-Br—2-C$_4$H$_2$S | 125–126.5 | 97 | Pale Yellow Prisms (Ethanol) | C$_{14}$H$_{10}$Br$_2$O$_2$S$_3$ | 464 (7) | 36.06 | 2.16 | |

| Substituent | | Analysis Found | | | $\nu$CO. | H NMR (CDCl$_3$)δ |
|---|---|---|---|---|---|---|
| R$_1$ | R$_2$ | C | H | N | cm$^{-1}$ | |
| C$_6$H$_5$ | C$_6$H$_5$ | 72.07 | 5.41 | | 1680, 1630 | 8.20–7.34 (m, 10, aromatic), 6.82 (s, 1, —CH—), 4.64 (s, 2, —CH$_2$), 2.59 (s, 3, —SCH$_3$) |
| C$_6$H$_5$ | 2-C$_4$H$_3$S | 63.54 | 4.79 | | 1700, 1680, 1645, 1625 | 8.10–7.06 (m, 8, aromatic), 6.82 and 6.70 (s, —CH—), 4.62 and 4.60 (s, 2, —CH$_2$), 2.54 (s, 3, —SCH$_3$) |
| C$_6$H$_5$ | 2-C$_5$H$_4$N | 68.57 | 5.19 | 4.39 | 1680, 1640 | 8.63 (br, d, i aromatic), 8.20–7.33 (m, 8, aromatic), 7 6.76 (s, 1, =CH—), 4.76, 4.60 (s, 2, —CH$_2$), 2.43 (s, 3 —SCH$_3$) |
| 2-C$_4$H$_3$S | 2-C$_4$H$_3$S | 54.80 | 4.06 | | 1670, 1620 | 7.96–7.03 (m, 6, aromatic), 6.70 (s, 1, =CH—), 4.60 (s, 2, —CH$_2$—) 2 50 (s 3, —SCH$_3$) |
| 2-C$_4$H$_3$O | 2-C$_4$H$_3$S | 57.78 | 4.20 | | 1690, 1670 1640, 1620 | 7.90–6.96 (m, 5, aromatic), 6.73 and 6.66 (s, 1, =CH—), 6.50 (m, 1, aromatic), 4.55 and 4.45 (s, 2, —CH$_2$—), 2.47 (s, 3, —SCH$_3$) |
| 2-C$_5$H$_4$N | 2-C$_5$H$_4$N | 64.42 | 4.84 | 9.37 | 1700, 1646 | 8.74–7.20 (m, 9, aromatic and vinylic), 4.83 (s, 2 —CH$_2$—), 2.60 (s, 3, —SCH$_3$) |

TABLE I-continued

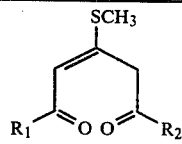

1,5-Enediones Derived from α-Oxoketene Dithioacetals

| $R_1$ | $R_2$ | | | | | |
|---|---|---|---|---|---|---|
| 2-C$_5$H$_4$N | 1-C$_4$H$_3$S | 59.67 | 4.51 | 4.72 | 1700, 1630 | 8.85–6.96 (m, 7, aromatic), 7.70 and 6.70 (s, 1, =CH—), 4.80 and 4.57 (s, 2, —CH$_2$—), 2.56 and 2.51 (s, 3, —SCH$_3$) |
| 2-BrC$_6$H$_4$ | 3-BrC$_6$H$_4$ | 47.59 | 3.14 | | 1690, 1640 | 8.15–7.15 (m, 8, aromatic), 6.22 (s, 1, —CH—), 4.48 (s, 2, —CH$_2$—), 2.50 (s, 3, —SCH$_3$) |
| 4-CH$_3$OC$_6$H$_4$ | 4-CH$_3$OC$_6$H$_4$ | 67.38 | 5.66 | | 1655 | 8.03, 7.91, 7.0, 6.90 (4d, 8, J = 9, OHz, aromatic), 7.0 (s, 1, =CH—), 4.22 (s, 2, —CH$_2$—), 3.90 and 3.85 (2s, 6, —OCH$_3$), 2.30 (s, 3, —CH$_2$) |
| 4-CH$_3$OC$_6$H$_4$ | CH$_3$ | 63.70 | 6.13 | | 1710, 1640 | 9.02, 7.96, 7.15 (3d, 4, J = 9.0 Hz, aromatic), 6.77, 6.13 (s, 1, =CH$_2$—) 4.45, 3.93 (s, 2, —CH$_2$—), 3.88 (s, 3, OCH$_3$), 2.49, 2.41 (s, 3, SCH$_3$) 2.34, 2.18 (s, 3, CH$_3$). |
| 2-C$_4$H$_3$S | 5-Cl—2-C$_4$H$_2$S | 49.27 | 3.35 | | 1665, 1623 | 7.82–6.50 (m, 4, thiophene), 6.63, 6.53 (m, 1, =CH—), 4.53, 4.43 (s, 2, —CH$_2$—), 2.45 (s, 3, —SCH$_3$ |
| 5-Br—2-C$_4$H$_2$S | 5-Br—2-C$_4$H$_2$S | 36.25 | 2.13 | | 1669,1620 | 7.52, 7.39, 7.06, 6.98, (4d, 4, J = 4.0 Hz, thiophene), 6.48 (s, 1, =CH—), 4.40 (s, 2, —CH$_2$), 2.47 (s, 3, —SCH$_3$) |

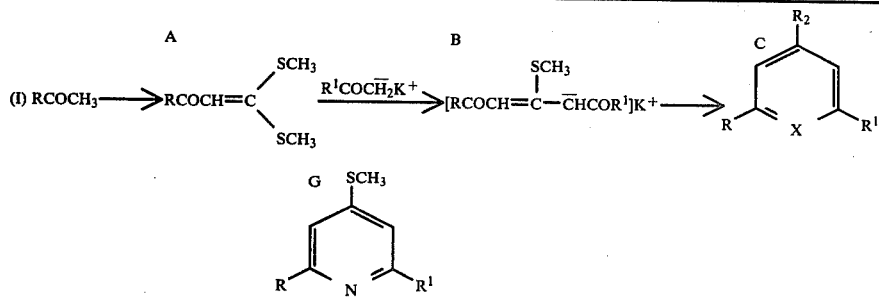

TABLE II

Substituted Pyridines Derived from α-Ketoketenedithioacetals (A)

| R | $R^1$ | MP °C. | Yield % | $M^{+a}$ |
|---|---|---|---|---|
| C$_6$H$_5$ | C$_6$H$_5$ | 105–107 | 81 | 277 |
| 4-CH$_3$OC$_6$H$_4$ | CH$_3$ | 69–70 | 70 | 245[b] |
| 4-BrC$_6$H$_4$ | 4-BrC$_6$H$_4$ | 115–116 | 85 | 435 |
| 4-CH$_3$OC$_6$H$_4$ | 4-CH$_3$OC$_6$H$_4$ | 90.5-91 | 48 | 337 |
| C$_6$H$_5$ | 2-C$_5$H$_4$N | 80–81 | 89 | 278 |
| 2-C$_5$H$_4$N | 2-C$_5$H$_4$N | 120–121 | 81 | 279 |
| 2-C$_5$H$_4$N | 2-C$_4$H$_3$S | 133–134 | 80 | 284 |
| 6-Br—2-C$_5$H$_3$N | 6-Br—2-CiH$_3$N | 184–185 | 31 | 437 |
| 2-C$_4$H$_3$S | 2-C$_4$H$_3$S | 115–116 | 99 | 289 |
| 2-C$_4$H$_3$S | 5-Cl—2-C$_4$H$_2$S | 115–116 | 72 | 323 |
| 2-C$_4$H$_3$O | 2-C$_4$H$_3$O | 96–97 | 64 | 257 |
| 2-C$_4$H$_3$O | 2-C$_4$H$_3$S | 95–97 | 74 | 273 |

[a] Relative Intensities, 100%,
[b] 93%.

As generally shown in reaction I, 2-Acetylpyridine (R=2-C$_5$H$_4$N) was converted into 3,3bis(methylthio)-1-(2-pyridinyl)-2-propen-1-one (product A where; R=2-C$_5$H$_4$N) using NaH/DMSO, CS$_2$ and CH$_3$I and was obtained as yellow needles (71%) from ethanol, m.p. 108°'''109° C., $v_{co}$1605 cm$^{-1}$, M.+ 225. This α-ketoketenedithioacetal (3.0 g, 0.013 mol) was added to a solution of 2-acetylpyridine (1.6 g, 0.013 mol) and postassium tert-butoxide (3.0 g, 0.027 mol) in dry THF (80 mL). After stirring for 3 hours at room temperature, ammonium acetate (10.0 g, 0.013 mol) and glacial acetic acid (80 mL) were added to the above solution which was then heated for 2 hours with continuous removal of THF. After cooling, addition of ice-water resulted in the separation of 2,6-di (2'-pyridinyl)-4-(methylthio)-pyridine (Product C where; R=R$^1$=2-C$_5$H$_4$N; R$^2$=SCH$_3$; X=N) which crystallized from ethanol:water as colorless needles, 2.0 g (79%), m.p. 120°–121° C., M.+ 279. Refluxing this product with an excess of Raney nickel (6 hr) in ethanol gave 2,2',2'''-terpyridinyl (Product C where; R=R$^1$=2-C$_5$H$_4$N; R$^2$=H; X=N) as cream prisms (60%) m.p. 84°–85° C., M.+ 233.2735 (100%).

This reaction sequence is also useful for pyridine ring annulation to a variety of cycloalkyl ketones. Reaction of Product A where R=4-CH$_3$OC$_6$H$_4$, with cyclohexanone under the above conditions gave Product D (X=N) as colorless needles (10%), m.p. 105°–106° C., M.+ 285 (100%). In addition quinquepyridine may also be obtained by this route. Reaction compound E (3.0 g, 0.013 mol) with 2-acetylpyridine (1.09 g, 0.0066 mol) and potassium tert-butoxide (3.0 g, 0.027 mol) in dry THF as above, gave 2,6-bis[2'-(4'-methylthio)-6'-(2''-pyridinyl)pyridinyl] pyridine (Product F as colorless flakes from DMF: 1.5 g (53%), mp 265°–266° C., M.+ 479.6271 (100%).

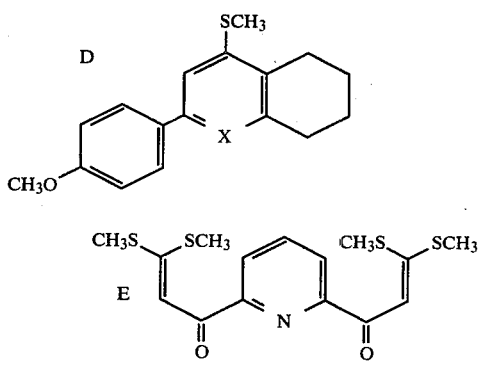

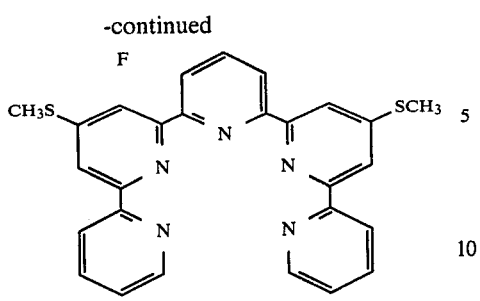

According to the invention, these 1,5-enediones provide a ready entry into a variety of substituted pyrylium salts. This new procedure overcomes the majority of the disadvantages of current procedures Z* and approaches the goal of a general synthesis.

This is illustrated by the preparation of 2-methyl-4-methylthio-6-(4-methoxyphenyl)pyrylium tetrafluoroborate (Product C where; R=4-CH$_3$OC$_6$H$_4$; R$^1$=CH$_3$; R$^2$=SCH$_3$; X=O$^+$·BF$_4$). Potassium tert-butoxide (5.04 g, 0.045 mol) was added to a stirred mixture of acetone (1.2 g, 0.02 mol) and the ketenedithioacetal (Product A where R=4-CH$_3$OC$_6$H$_4$; 5.0 g, 0.02 mol). An initial yellow suspension changed over a 16 hour reaction period into a dense green precipitate of the potassium salt of Product B (R=4-CH$_3$OC$_6$H$_4$; R$^1$=CH$_3$). This was collected and added to an ice-cold 4% HCl solution (200 mL) giving the corresponding 1,5-diketone as a thick suspension which was collected and then stirred in dichloromethane (40 mL) with HBF$_4$(20 mL of 48% solution) for 4 hours at 50° C. *[For Reviews see: Perst, H. "Qxonium Ions in Organic Chemistry", Verlag Chemie, Weinheim, 1971; Balaban, A. T.; Schroth, W.; Fischer, G. *Advan. Heterocyclic Chem.* 1969, 10, 241].

The yellow pyrylium salt separated during this period and, after addition of water (20 mL) the pyrylium salt was collected. It crystallized from acetic acid as light yellow needles (70%) m.p. 207°-210° C. decom. Use of cyclohexanone as the ketonic component in the above reaction gave 2-(4-methoxyphenyl)-4-methylthio-5,6,7,8-tetrahydrobenzopyrylium tetrafluoroborate (Product D X=O$^+$·BF$_4$) as yellow-green needles (40%) from acetic acid, m.p. 245°-250° C. decomp. Aromatic substituents were readily introduced into the 2,6-positions e.g., use of 4-methoxyacetophenone (as starting compound in I where; R$^1$=4- CH$_3$OC$_6$H$_4$) in the above reaction gave 2,6-bis(4-methoxyphenyl)-4-(methylthio)pyrylium tetrafluoroborate (C;R=R$^1$=4-CH$_3$OC$_6$H$_4$; R$^2$=SCH$_3$; X=O$^+$·BF$_4$) as yellow prisms (53%) from acetic acid, m.p. 288°-290° C. decomp. In some cases the yield approaches quantitive as in the formation of 2,6-diphenyl-4-(methlthio)pyrylium tetrafluoroborate (C;R=R$^1$=C$_6$H$_5$; R$^2$=SCH$_3$; X=O$^+$·BF$_4$) which was isolated as pale-green needles (93%) from 1,2-dichloroethane, mp 253°-255° C. The variety of aryl and heterocyclic ketones, either as the α-ketoketenedithioacetal component or the ketonic component, which take part in this reaction allows the introduction of a wide variety of substituents in the 2- and 6- positions. See Rastogi, R. R.; Kumar, A., Ila, H., Junjappa, H. J. *Chem.Soc. Perkin I* 1978, 549; Thuillier, A.; Vialle, J. Bull Soc.Chim. France 1962, 2182, 2187; Thuillier, A., Vialle, J. *Bull.Soc. Chim. France* 1962 2194

Alternatively, this synthesis may be accomplished in a "one-pot" reaction. In this case, the 1,5-diketone is not isolated and the tetrafluoroboric acid is merely added to the initial THF reaction mixture. The product is contaminated with KBF$_4$ which may be removed by washing with hot water, resulting in a reduced yield of the pyrylium salt. This procedure is best with aromatic substituents in the 2- and 6- positions. The 4-methylthio group in C (X=O$^+$·BF$_4$) similarly to the 4-chloro and 4-methoxy groups, is susceptible to displacement by nucleophiles such as secondary amines. See R. M. Ankee and A. H. Cook, *J. Chem. Soc.* 1946, 117; L. C. King and F. J. Ozog, *J. Org. Chem.* 1955, 20, 448.

This synthesis offers many advantages over those currently used for the preparation of the corresponding 4-(substitutedthio) pyrylium salts. As pyrylium salts of the corresponding 1, 5diketones are readily converted into thiopyrylium and seleninium salts, these ring systems are now readily available with similarly diverse substitution patterns.

A more detailed version of equation I is shown at equation II that more clearly indicates the reaction scheme of the invention.

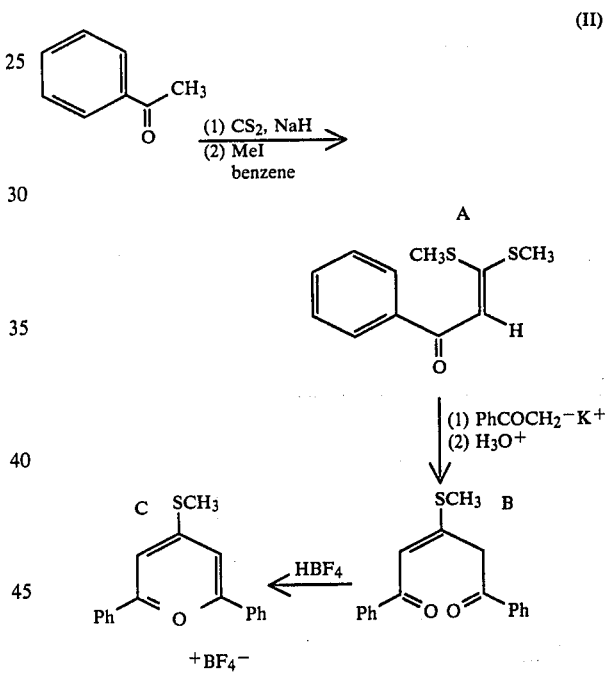

(II)

The three stage reaction which yields products A, B and C respectively is as follows:

Preparation of
3,3-Bis(methylthio)-1-phenyl-2-propen-1-one(-Producta)

Acetophenone (6.0 g, 0.05 mol) was mixed with sodium hydride (4.2 g of 57% oil suspension, 0.1 mol), carbon disulfide (6.0 g, 0.075 mol), MeI (22.5 g, 0.15 mol) and dry benzene (80 ml) Dimethylacetamide was added dropwise (10 mL) while cooling and the mixture was stirred overnight at room temperature. Crushed ice was then added to the benzene solution with care (unreacted NaH might be present), the benzene extract was dried (MgSO$_4$) and evaporated under reduced pressure to give pale yellow crystals. Crystallization from methanol gave pale yellow needles: 6.0 g (58%) m.p. 90°-92° C. (lit.m.p 93° C.); IR (KBr)$\nu_{CO}$1600 cm$^{-1}$; NMR (CDCl$_3$)δ7.9-7.5 (m, 5, aromatic), 6.76 (s,1, vinylic) 2.56

(s, 3,SCH₃), 2.52 (s,3, SCH). See A. Thuiller and J. Vialle, *Bull. Soc. Chem. Fr.* 1959, 1398.

Preparation of 1,5-Diphenyl-3-methylthiopent-2-en-1,5-dione (Product B)

Ketene dithioacetal (Product A) (2.0 g, 0.0089 mol) was added to a solution of acetophenone (1.07 g, 0.0089 mol) and potassium tert-butoxide (2.0 g, 0.0178 mol) in dry THF (20 mL). The temperature of the reaction mixture was raised to 60° C. and the mixture was stirred for 1 hour during which time an orange-red precipitate formed. This was collected and added to an ice-cold HCl solution (4% acid) and the oily material which separated allowed to crystallize. The brown solid was collected and recrystallized from benzene: petroleum ether (b.p. 80°–100° C.) from which it separated as pale-yellow prisms: 1.8 g (70%), m.p 106°–108° C: IR (KBr)$\nu_{CO}$ 1680, 1630 cm$^{-1}$; NMR (CDCl₃) δ8.0–7.56 (m, 10, aromatic), 6.82 (s,1, vinylic), 4.64 (s,2,CH₂), 2.59 (s,3,SCH₃); M.+ 296 (7%).

Anal. Calcd for C₈H₁₆O₂S; C,72.96; H,5.44. Found: C, 72.82; H, 5.41.

Preparation of 2,6-Diphenyl-4-methylthiopyrylium Tetrafluoroborate (Product C )

The above pentendione(Product B) (3.5 g, 0.012 mol) was dissolved in 1,2-dichloroethane (30 mL), tetrafluoroboric acid (20 mL of 48% solution) was added and the mixture heated under reflux for 30 minutes. After cooling to room temperature, the green crystals were collected and the mother liquor was refluxed for and additional 30 minutes, yielding a further amount of product on cooling: 4.0 g (93%). It crystallized from 1,2-dichloroethane as pale green needles, m.p. 253°–255° C: IR (KBr) 1601 (C=O+) cm$^{-1}$; NMR (CF₃COOH) δ8.0–7.5 (m, 10, aromatic); δ 2.97 (s,3, SCH₃); M.+279 (74%).

Anal. Calcd for C₁₈H₁₅OS. BF₄: C, 59.03; H, 4.12. Found: C, 59.16; H, 4.18.

The following additional examples are disclosed for a better understanding of the invention:

EXAMPLE 1

Preparation of 2,6-Diphenyl-4-(methylthio)pyrylium Tetrafluoroborate 3,3. Bis (methylthio)-1-phenyl-2-propen-1-one, prepared by the method described by A. Thuillier and J. Vialle, *Bull. Chim. Soc. France*, page 1398 (1959) and also by I. Shahak and Y. Sasson, *Tetrahedron Letters*, page 4207 (1973), (2.0 g, 0.0089 mol) was added to a solution of acetophenone (1.07 g, 0.0089 mol) and potassium tert-butoxide (2.0g, 0.0178 mol) in dry THF (20 ml). The solution was stirred overnight at room temperature and the resultant red-brown precipitated was collected and added to an ice-cold HCl solution (4% acid) and the oily material that separated was allowed to crystallize from benzene:petroleum ether(b.p 80°–100° C.) from which 1,5-diphenyl-3-methylthio-2-penten-1,5-dione separated as pale yellow prisms: 2.0 g(76%), m.p. 106°–108° C; IR (KBr) $\nu_{CO}$ 1630, 1630cm$^{-1}$; λmax (CH₃OH) nm (logε) 319 (4.19), 241 (4.22); NMR (CDCl₃) 8.20–7.34 (m, 10, aromatic), 6.82 (s, 1, vinylic), 4.64 (s,2,CH₂), 2,59 (s, 3, SCH₃) M.+ 296 (17).

Anal. Calcd for C₁₈H₁₆O₂S: C, 72.96; H, 5.44. Found: C, 72.82; H, 5.41.

This 1,5-enedione (3.50g, 0.0118 mol) was added to a solution of tetrafluoroboric acid (20 ml of 48% aqueous solution) and 1,2-dichloroethane (30ml) and the mixture heated under reflux for 30 minutes. After cooling to room temperature, the green crystals were collected and the mother liquor was refluxed for an additional 30 minutes, yielding further product on cooling.

Recrystallization from 1, 2-dichloroethane afforded 2,6-diphenyl-4-(methylthio)pryrylium tetrafluoroborate as pale green needles: 4.0 g (93%), m.p. 253°–255° C.; IR (KBr) 1601 (C=O+)cm$^{-1}$, λmax (CH₃OH nm (logε) 336 (3.89) 266 (4.02); NMR (CF₃COOH) 8.0–7.50 (m, 12, aromatic), 3.0 (s, 3, SCH₃); M.+ (C₁₈H₁₅OS) 279 (74).

Anal. Calcd for C₁₈H₁₅BF₄OS: C, 59.03; H, 4.12. Found: C, 59.16; H, 4.18.

EXAMPLE 2

2,6-di-(4-methoxyphenyl)-4-(methylthio)pyrylium Tetrafluoroborate 3,3-Bis(methylthio)-1-(4-methoxphenyl)-2-propen-1-one (4.0 g, 0.02 mol), prepared by the method of I. Shahak and Y. Sasson, *Tetrahedron Letters*, page 4207 (1973), was added to a stirred mixture of potassium tert-butoxide (5.04g, 0.045 mol.) and 4-methoxyacetophenone (3.0 g, 0.02 mol.) in freshly distilled THF (50 ml). The resulting bright orange suspension was stirred at room temperature for 8 hours. The solid was then collected by filtration and added to ice-cold hydrochloric acid (4% aqueous solution). The orange oil that initially separated rapidly solidified. The enedione was collected and and dissolved in 1,2-dichloroethane (25ml). Tetrafluoroboric acid (5 ml, 48%) was added and the mixture heated under reflux for 30 minutes. After cooling the orange solid was collected and yellow prisms were obtained on crystallization from dichloroethane: 4.5 g (53%), m.p. 288°–290° C. (decomp); NMR (DMSO-d₆) δ3.0 (s, 3, SCH₃), 3.88 (s, 6, OCH₃), 7.27 (d,4 J=9.0 Ha), 8.30 (d,4,J=9.0 H₃), 8.32 (s,2, aromatic).

Anal. Calcd for C₂₀H₂₉O₃SBF₄: C, 56.35; H, 4.49. Found:
C, 56.20; H, 4.52.

EXAMPLE 3

2-Methyl-4-methylthio-6-(4-methoxphenyl)pyrylium Tetrafluoroborate

To a stirred solution of 3,3-bis(methylthio)-1-(4-methoxyphenyl)-2-propen-1-one (10.0g, 0.042 mol) prepared by the method described by I. Shahak and Y. Sasson, *Tetrahedron Letters*, page 4207 (1973), and acetone (2.4g, 0.043 mol) in freshly distilled THF was added potassium tert-butoxide (10.1 g, 0.09 mol). The thick green mixture was stirred at room temperature overnight. The potassium salt was then collected and added to iced water (150 ml). This suspension was stirred with gradual addition of hydrochloric acid (4%) until a cream precipitate formed. 1-(4-Methoxyphenyl)-3-methylthio-2hexen-1, 5-dione was collected and recrystallized from methanol diethyl ether giving colorless needles: 4.6 g (42%), m.p. 105°–107° C.; IR(KBr)$\nu_{co}$1710, 1640cm$^{-1}$; M.+ 264 (18).

Anal. Calcd for C₁₄H₁₆O₃S: C, 63,61; H,6.10. Found; C, 63.70; H, 6.13.

To a solution of this 1-(4-methoxphenyl)-3-methylthio-2-hexen-1, 5-dione (2.0 g, 7.57 mmol) in 1,2-dichlorethane (20ml) was added tetrafluoroboric acid (10 ml, 48%). The mixture was stirred for four hours at 50° C. during which time a dense yellow solid formed. After addition of water (25 ml) and filtration, crystallization from acetic acid gave pale yellow needles of 2-methyl-4-methylthio 6-(4-methoxyphenyl)pyrylium tetrafluoroborate; 2.2 g (87%), m.p. 207°–210° C. (decomp), IR (KBr)$\nu_{CO}$+1625 cm$^{-1}$; NMR(DMSO-d$_6$) δ8.34 (s,1, aromatic), 8.29 (d,2, J=9.0 Hz, aromatic), 7.80 (br. 3, 1, aromatic), 7.18 (d, 2, J=9.0 Hz, aromatic) 3.97 (s, 3, OCH$_3$), 2.91 (s, 3, SCH$_3$), (s, 3, CH$_3$); M.+ 246 (100).

Anal. Calcd for C$_{14}$H$_{15}$O$_2$SBF$_4$: C, 50.32; H, 4.53. Found: C, 50.12; H, 4.55.

EXAMPLE 4

4-Methylthio-2-(4-methoxyphenyl)-5,6,7,8-tetrahydrobenzo[b]pyrylium Tetrafluoroborate To a stirred mixture of potassium tert-butoxide (10.1 g, 0.09 mol) and cyclohexanone (3.90 g 0.04 mol) in freshly distilled THF was added 3,3-bis(methylthio)-1-(4-methoxphenyl)-2-propen-1-one (10.0 g, 0.039 mol) prepared as described above. The mixture rapidly became very deep red and was stirred overnight. Addition of the cooled reaction mixture to ice cold hydrochloric acid (200 ml, 4%) gave a yellow precipitate that was collected and washed with ice cold THF before further use (7.3 g, 62%). Crystallization from ethanol gave yellow prisms with considerable decomposition: mp 189°–10° C. (decomp).

The unpurified enedione (5.0 g, 0.0164 mol) was stirred in 1,2-dichloroethane (30 ml) together with tetrafluoroboric acid (20 ml, 48%). The mixture was stirred at room temperature over a period of five hours during which it became orange. Addition of water (25 ml) and filtration gave a yellow solid that crystallized from acetic acid as yellow needles: 4.05 g (74%), m.p. 246°–250° C. (decomp): NMR (DMSO-d$_6$) δ8.42 (s,1, aromatic), 8.62 (d, 2, J=9.0 Hz, aromatic), 7.55 (d,2, J=9.0 Hz, aromatic), 4.22 (s, 3, OCH$_3$), 3.27, 2.78, 2.20 (br. s, 8, cyclohexyl).

Anal. Calcd for C$_{17}$H$_{19}$O$_2$SBF$_4$: C, 54.65; H, 5.12. Found: C, 54.12; H, 5.10.

EXAMPLE 5

General Procedure for the Preparation of 2,6-Disubstituted-4-(methylthio) thiopyrylium Salts To a solution of the corresponding pyrylium tetrafluoroborate (0.003 mol) in acetone (60 ml), sodium sulfide monohydrate (0.015 mol) in water (10 ml) was added slowly. The solution was stirred for one hour, a purple color developing during this time. Tetrafluoroboric Acid (10 ml of a 48% aqueous solution) was added and the reaction mixture stirred for two additional hours. The brown precipitate was collected and recrystallized from acetic acid.

Using this procedure, 2,6-diphenyl-4-(methylthio)thiopyrylium tetrafluoroborate was obtained in 73% yield, m.p. 230°–232° C. (decomp) after crystallization from acetic acid from which it separated as brown needles; λmax (CH$_3$OH) nm (log ϵ) 358 (3.99), 296 (3.93), 239 (4.35), 225 (4.35); NMR (CF$_3$COOH) δ8.4 (s,2, aromatic), 8.27–7.62 (m, 10, aromatic), 3.0 (s,3, SCH$_3$); Mo+ (C$_{18}$H$_{15}$BF$_4$S$_4$) 382 (7).

Anal. Calcd for C$_{18}$H$_{15}$BF$_4$S$_2$: C, 56.56; H, 3.95. Found C, 56.17; H, 3.97.

Similarly, 2,6-di-(4-methoxyphenyl)-4-(methylthio) thiopyrylium tetrafluoroborate is obtained in 48% yield, m.p. 198°–200° C., as fine orange needles after crystallization from acetic acid; NMR ("Unisol") δ8.30 (s, 2, aromatic), 8.02 (d, 4, J=9.0 Hz, aromatic), 7.18 (d, 4, J=9.0 Hz, aromatic), 3.95 (s, 3, OCH$_3$), 3.02 (s, 3, SCH$_3$).

Anal. Calcd for C$_{20}$H$_{18}$BF$_4$O$_2$S$_2$: C, 54.31; H, 4.33. Found: C, 53.99; H, 4.40.

While specific embodiments of the invention have been shown and described in detail to illustrate the application of the principles of the invention, it will be understood that the invention may be embodied otherwise without departing from such principles.

What is claimed is:

1. 2,6-di-(4-methoxyphenyl-4(methylthio)pyrylium tetrafluoroborate.
2. 2-methyl-4-methylthio-6-(4-methoxyphenyl)-pyrylium tetrafluoroborate.
3. 4-methylthio-2-(4-methoxphenyl)-5,6,7,8-tetrahydrobenzo-[b] pyrylium tetrafluoroborate.

* * * * *